US00PP15075P2

(12) United States Plant Patent
Zary

(10) Patent No.: US PP15,075 P2
(45) Date of Patent: Aug. 10, 2004

(54) HYBRID TEA ROSE NAMED 'JACFREPU'

(50) Latin Name: *Rosa hybrida*
Varietal Denomination: JACfrepu

(75) Inventor: Keith W. Zary, Somis, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/697,594

(22) Filed: Oct. 29, 2003

(51) Int. Cl.[7] ..... A10H 5/00
(52) U.S. Cl. ..... Plt./132
(58) Field of Search ..... Plt./132

*Primary Examiner*—Anne Marie Grunberg
*Assistant Examiner*—S. B. McCormick-Ewoldt
(74) *Attorney, Agent, or Firm*—Klarquist Sparkman LLP

(57) ABSTRACT

Hybrid tea rose plant having vigorous upright growth; large, fragrant flowers; resistance to rust and powdery mildew; and dark, glossy foliage.

1 Drawing Sheet

Genus and species: *Rosa hybrida*.
Variety denomination: 'JACfrepu'.

ORIGIN OF THE INVENTION

The present invention relates to a new and distinct variety of a hybrid tea rose plant named 'JACfrepu' which was originated by me by crossing the variety 'JACjel' (Sunbright), U.S. Plant Pat. No. 4,438, with the variety 'KEIbian' (French Perfume), U.S. Plant Pat. No. 8,476.

BACKGROUND OF THE INVENTION

The primary objective of this breeding was to produce a new rose variety having the strong yellow flower color and good stem length of the female parent combined with the fragrance of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Vigorous upright growth.
2. Large, fragrant flowers of yellows and pinks.
3. Resistance to rust and powdery mildew.
4. Dark, glossy foliage.

Asexual reproduction of this new variety by budding, as performed at Wasco, Calif., shows that the foregoing and all other characteristics and distinctions come true to form and are established and transmitted through succeeding propagations.

COMPARISON WITH PARENTS

The subject variety differs from 'JACjel' in flower color (yellow for Sunbright, yellow and pink for 'JACfrepu') and from 'KEIbian' in flower color, peduncle length, foliage color and fragrance (fruity for 'JACfrepu' and sweet damask for 'KEIbian').

COMPARISON WITH SIMILAR VARIETY

The subject variety is most similar to 'KEIbian' from which it differs as noted above.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—'JACgel' (Sunbright), U.S. Plant Pat. No. 4,438.
*Pollen parent.*—'KEIbian' (French Perfume), U.S. Plant Pat. No. 8,476.

FLOWER

Observations made from plants commencing at two years of age grown in garden environments at Somis and Wasco, Calif.

Blooming habit: Continuous.
Bud:
*Size.*—About 40–50 mm long and 25–30 mm in diameter when the petals start to unfurl.
*Form.*—The bud form is long, pointed ovoid.
*Color.*—When sepals first divide, bud color is Yellow Group 8C often with Red Group 51B and Red Group 52A on the outer guard petals. When half blown, the inner one half of the petals on their upper sides are Yellow Group 6C while the lower sides of such petals are Yellow Group 6C at their base but become increasingly Yellow 5D toward their apex. The outer one half of the petals on their upper and lower surfaces are Yellow Group 6C at their base, Yellow Group 8D in their mid portion and Red Group 50B at their apex.

*Sepals.*—Color: Upper surface: Green Group N 138B with underlay of Red Group 53C. Lower surface: Yellow-Green Group 144A with underlay of Greyed-Red Group 181A. Length: 30–33 mm. Width: 8–10 mm. Shape: Subulate. Surface texture: Hoary. There are three normally appendaged sepals. There are two unappendaged sepals with hairy edges.

*Receptacle.*—Color: Green Group 139C. Shape: Funnel. Size: Medium, about 10 mm long×7 mm wide. Surface: Smooth.

*Peduncle.*—Length: Medium, averaging about 50–55 mm. Surface: Smooth with occassional glands. Color: Yellow-Green Group 146B to C with under bright light, some Greyed-Red Group 183A coloration. Strength: Stiff, erect.

Bloom:

*Size.*—Large. Average open diameter is about 12–13 cm.

*Borne.*—Singly.

*Stems.*—Strength: Strong. Average length is about 45–50 cm with a diameter of 7–8 mm.

*Form.*—When first open: High centered. Permanence: Retains its form to the end, outer petal edges curl slightly.

*Petalage.*—Number of petals under normal conditions: 30–35.

*Color.*—The upper sides of the petals are Yellow Group 6C on the inner one half of the petals changing to Yellow Group 8D in the center and to Red Group 50B at their apex. The reverse sides of the petals are Yellow Group 6C at the base becoming increasingly Yellow Group 5D toward the middle, then Yellow Group 8D and finally Red Group 50B at the apex. The base of each petal has a small 5 mm×5 mm color spot of Yellow Group 6A. The major color on the upper side is Yellow Group 8D.

*Variegations.*—None.

*Discoloration.*—The general tonality at the end of the first day: No change. At the end of the third day: Little change. Further aging: The colors finish by a general fading with petal drop by day 7.

*Fragrance.*—Strong, fruity.

Petals:

*Texture.*—Thick, leathery.

*Shape.*—Round.

*Surface.*—Smooth.

*Margin.*—Entire. Apex Shape: Obtuse. Base Shape: Rounded.

*Form.*—Tips slightly recurved.

*Arrangement.*—Irregular.

*Petaloids.*—Number: 3–7 Color: Yellow Group 6C.

*Persistence.*—Petals drop off cleanly before drying.

*Lastingness.*—On the plant: Fair (about 6–7 days). As a cut flower: Fair (about 8 days).

Reproductive parts:

*Stamens.*—Number: 60–70. Length: 3 mm. Anthers: Length: 10–12 mm. Color: Yellow-Orange Group 15C. Arrangement: Regular around styles. Filaments: Color: Yellow Group 12B. Length: 8–9 mm. Pollen: Color: Yellow-Orange Group 22B.

*Pistils.*—Number: 40–45. Length: 4–5 mm. Styles: Color: Red Group 46D. Length: 3–4 mm. Stigmas: Color: Greyed-Yellow Group 161B. Length: 1 mm.

*Hips.*—Not observed.

PLANT

*Form.*—Bush.

*Growth.*—Vigorous, upright, branching.

*Age at maturity.*—Two years.

*Mature plant.*—Height: 150–170 cm. Width: 70–80 cm.

*Rootstock.*—Dr. Huey.

Foliage: Number of leaflets on normal mid-stem leaves: 5 or 7.

*Size.*—About 150 mm long×120 mm wide.

*Quantity.*—Abundant.

*Color.*—New foliage: Upper side: Greyed-Purple Group 183A. Lower side: Greyed-Purple Group 183A. Old foliage: Upper side: Green Group 136A. Lower side: Yellow-Green Group 146B but often with a background of Greyed-Red Group 178A.

Leaflets:

*Size.*—About 50 long×35 wide.

*Shape.*—Broadly oval.

*Base shape.*—Rounded to slightly obique.

*Apex shape.*—Acuminate.

*Texture.*—Leathery, glossy.

*Edge.*—Serrated.

*Serrations.*—Single, small.

*Petiole.*—Color: Yellow-Green Group 147C.

*Petiole rachis.*—Color: Yellow-Green Group 147C. Underside: Rough, one prickle and glands.

*Auricle shape, if present.*—None.

*Stipules.*—Length: 15–17 mm, serrated, bearded and with glands.

*Disease resistance.*—Resistant to mildew and rust and susceptible to blackspot under normal growing conditions.

*Pest resistance.*—Not observed.

*Vein color.*—Same as leaf color.

*Venation pattern.*—Reticulate.

Wood:

*New wood.*—Color: Yellow-Green Group 146C — with Greyed-Red Group 178B as a background. Bark: Smooth.

*Old wood.*—Color: Yellow-Green Group 146A. Bark: Smooth.

Prickles:

*Quantity.*—On main canes from base: 12 to 15 per 15 cm. On laterals from main canes: 12 to 15 per 15 cm.

*Form.*—Hooked downward.

*Length.*—10–12 mm.

*Color when young.*—Greyed-Red Group 178B.

*Color when mature.*—Greyed-Orange Group 168D.

Small prickles:

*Quantity.*—On main stalks: None. On laterals: None.

Winter hardiness: Hardy to Zone 5.

I claim:

1. A new and distinct variety of rose plant of the hybrid tea class, substantially as herein shown and described, characterized particularly by its vigorous upright growth; large, fragrant flowers; resistance to rust and powdery mildew; and dark, glossy foliage.

* * * * *

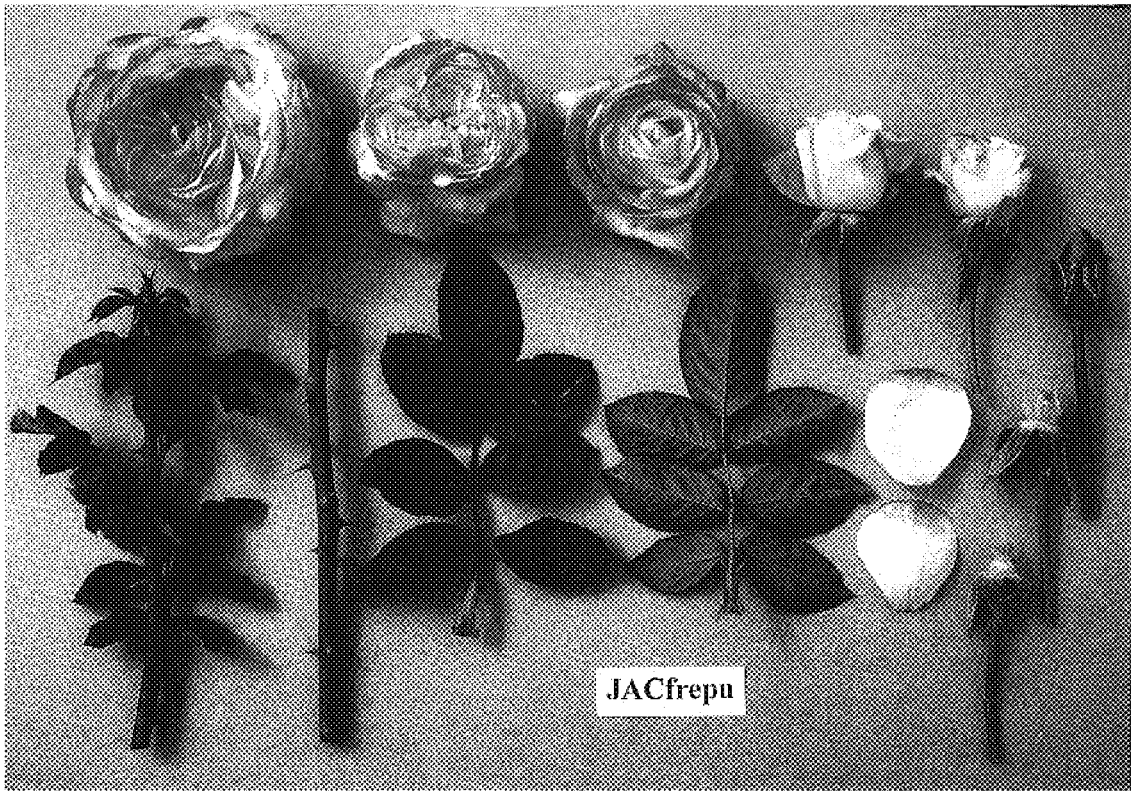
JACfrepu